(12) United States Patent
Schreiber et al.

(10) Patent No.: US 9,743,964 B2
(45) Date of Patent: Aug. 29, 2017

(54) INTRAMEDULLARY NAIL, PARTICULARLY LOCKABLE INTRAMEDULLARY NAIL, AND DEVICE FOR FIXATING THE INTRAMEDULLARY NAIL IN A HOLLOW BONE

(75) Inventors: Ulrich Schreiber, Munich (DE); Stefan Eichhorn, Deisenhofen (DE)

(73) Assignee: OT MEDIZINTECHNIK GMBH, Munich (DE)

( * ) Notice: Subject to any disclaimer, the term of this patent is extended or adjusted under 35 U.S.C. 154(b) by 1921 days.

(21) Appl. No.: 12/601,406

(22) PCT Filed: May 20, 2008

(86) PCT No.: PCT/EP2008/004048
§ 371 (c)(1),
(2), (4) Date: Mar. 3, 2010

(87) PCT Pub. No.: WO2008/141805
PCT Pub. Date: Nov. 27, 2008

(65) Prior Publication Data
US 2010/0179550 A1    Jul. 15, 2010

(30) Foreign Application Priority Data

May 23, 2007  (DE) .................. 10 2007 023 891
Oct. 24, 2007  (DE) .................. 10 2007 051 136
Mar. 18, 2008  (DE) .................. 10 2008 014 697

(51) Int. Cl.
*A61B 17/56* (2006.01)
*A61B 17/72* (2006.01)
(Continued)

(52) U.S. Cl.
CPC ...... *A61B 17/7241* (2013.01); *A61B 17/1725* (2013.01); *A61B 17/725* (2013.01); *A61B 17/8625* (2013.01)

(58) Field of Classification Search
CPC ............ A61B 17/1725; A61B 17/7241; A61B 17/725
(Continued)

(56) References Cited

U.S. PATENT DOCUMENTS 6,004,324 A     12/1999  Gahr et al.
6,106,528 A *    8/2000  Durham et al. ................. 606/64
(Continued)

FOREIGN PATENT DOCUMENTS

DE           296 20 327 U1      3/1998
DE       10 2005 009 347 A1     9/2006
(Continued)

OTHER PUBLICATIONS

English language abstract of JP 2005-270503.
English language machine translation of JP 2005-270503.

*Primary Examiner* — Jan Christopher Merene
*Assistant Examiner* — Atiya Mahmud
(74) *Attorney, Agent, or Firm* — Abel Law Group, LLP (57) ABSTRACT

Described is a locking intramedullary nail for insertion in the medullary cavity of hollow bones for treating bone fractures or for joint stiffening. The nail comprises an oblong shaft having at least one holder for a locking screw. In the region of an opening a roller or ball-shaped sleeve having a bore for receiving the locking screw is arranged. The sleeve which is supported in the shaft in a freely pivotable manner can be locked in a positionally stable manner in the shaft. This affords the ability to introduce the locking screws during the implantation of the intramedullary nail at an optimum angle for the respective anatomical or pathological situation of the patient and to subsequently lock it permanently at a constant angle.

5 Claims, 4 Drawing Sheets

(51) Int. Cl.
    *A61B 17/17*    (2006.01)
    *A61B 17/86*    (2006.01)

(58) Field of Classification Search
    USPC .................................................. 606/62–68
    See application file for complete search history.

(56) References Cited

U.S. PATENT DOCUMENTS

| | | | |
|---|---|---|---|
| 6,235,031 B1* | 5/2001 | Hodgeman et al. | 606/64 |
| 2002/0032445 A1* | 3/2002 | Fujiwara | 606/67 |
| 2002/0173792 A1 | 11/2002 | Severns et al. | |
| 2004/0059329 A1* | 3/2004 | Zander | 606/53 |
| 2005/0010223 A1* | 1/2005 | Gotfried | 606/62 |
| 2005/0234457 A1* | 10/2005 | James et al. | 606/69 |
| 2006/0095040 A1* | 5/2006 | Schlienger et al. | 606/73 |
| 2007/0233102 A1* | 10/2007 | Metzinger | 606/62 |
| 2007/0233103 A1 | 10/2007 | Metzinger | |
| 2007/0233104 A1* | 10/2007 | Metzinger | 606/62 |
| 2007/0270846 A1 | 11/2007 | Metzinger | |
| 2007/0276382 A1* | 11/2007 | Mikhail et al. | 606/62 |
| 2008/0077142 A1 | 3/2008 | James et al. | |
| 2009/0216283 A1 | 8/2009 | Gradl | |

FOREIGN PATENT DOCUMENTS

| | | |
|---|---|---|
| DE | 20 2006 017 194 U1 | 1/2007 |
| EP | 1 839 608 A2 | 10/2007 |
| JP | 2005-270503 A | 10/2005 |
| WO | 2004/096067 A2 | 11/2004 |

\* cited by examiner

INTRAMEDULLARY NAIL, PARTICULARLY LOCKABLE INTRAMEDULLARY NAIL, AND DEVICE FOR FIXATING THE INTRAMEDULLARY NAIL IN A HOLLOW BONE

BACKGROUND OF THE INVENTION

1. Field of the Invention

The invention relates to an intramedullary nail and a device for fixating or fixing the intramedullary nail in a hollow bone according to the preambles of the independent patent claims.

2. Discussion of Background Information

Intramedullary nails and in particular lockable intramedullary nails are a known implement for the treatment fractures of long hollow bones, wherein the intramedullary nails are introduced into the medullary cavity of the damaged bone for mechanically bridging the bone lesion. With the so-called locking intramedullary nails, locking screws which are inserted for bridging and/or connecting the bone and the locking nail, particularly across or in the bone and the locking nail or parts thereof, serve to secure the connection between the bone and the locking nail against any displacement, in particular a displacement of the locking nail, in the direction of the bone axis, as well as against any rotation, particularly a rotation of the locking nail, as regards the bone axis.

In presently available common intramedullary nails, the locking screws are placed in fixed positions in discrete openings in the intramedullary nail. In this case, normally, the locking screws are arranged in the intramedullary nail in a substantially radial manner, however, the locking screws can—as for example in the proximal Femur—also be arranged at a predetermined angle of inclination with respect to the longitudinal axis of the intramedullary nail.

The placement of the locking screws in the intramedullary nail which is placed in the hollow bone hereby requires great experience on behalf of the surgeon so as to precisely position and fixate or fix the intramedullary nail. The surgeon has practically no possibility to correct even a slight misalignment of the locking screw during the surgery or operation.

In any case, hitherto, it has not been possible to adjust the position and the angle of the bores for the locking screws and their position as regards the individual anatomic situation resulting from the injury during surgery. It would, however, in many cases be advantageous to be able to vary the angle of the locking screws which penetrate through the intramedullary nail during surgery, in order to reposition fracture fragments or to adapt the fracture fragments in anatomically correct positions. Subsequently, the locking screws should be able to be blocked in an angularly stable manner in their determined positions.

The object of the present invention is to propose a further intramedullary nail, in particular a locking intramedullary nail (in the following also referred to as an intramedullary nail).

A further object of the invention is to propose an apparatus for fixing an intramedullary nail in a hollow bone.

SUMMARY OF THE INVENTION

The object according to the invention is solved by an intramedullary nail or a locking intramedullary nail or an apparatus for facilitating the fixation of the intramedullary nail in a bone, respectively, having the features of the independent claims.

Accordingly, a sleeve is arranged and/or supported in the shaft or at the shaft in an area of at least one opening of the intramedullary nail, wherein the sleeve is alignable, or moveable, or slideable, or pivotable in at least one spatial direction, for example in a direction perpendicular to the longitudinal axis of the bone or the intramedullary nail shaft and/or in a plane, particularly a plane comprising the aforementioned direction. The sleeve has an opening or a bore for receiving one locking screw or several ones of such locking screws or other locking devices. After insertion of the locking screw(s) in the shaft, the sleeve is locked or blocked or arrested, respectively, again.

In doing so, the pivotability of the sleeve or its non-pivotability after locking or blocking can be determined with respect to or can be attributed to a permitted or prohibited movement, particularly an inclinability or rotatability, of a virtual axis or line definable with respect to the sleeve. This axis can be a longitudinal or symmetrical axis of the opening or the bore of the sleeve.

According to the invention, the sleeve can be a device having at least one prepared or prefabricated through hole for the locking screw. The term "sleeve" refers to any structure that a person skilled in the art would normally relate to this term. However, according to the invention, also every device which does not have a prefabricated through hole but in which a passage for the locking screw is formed upon insertion of the locking screw or optionally even by the insertion itself can be encompassed by the term "sleeve".

According to the invention, the "sleeve" therefore also relates to a material or compound, in particular a thermosetting material or compound, such as bone cement, which allows an alignment of the locking screw(s) moved therethrough at an early, first point in time, but, however, does not allow such an alignment at a second, later point in time. According to the invention, also an arrest by means of a material which can take on different forms at different environmental temperatures and which can expand or contract under heat, shall be understood as an arresting device or a sleeve as long as the arresting effect is effected or favoured by means of these material characteristics.

The sleeve can, for example, be a roller having a roller axis which is, for example, perpendicular to the longitudinal axis of the shaft of the locking nail. However, the sleeve has preferably a spherical form so that it is supported in the shaft while being freely pivotably in all spatial axes.

The sleeve can be composed of several parts and/or of several materials (composite). For example, a synthetic, resin or plastic ring can be used as a part of the sleeve. It can advantageously prevent an unintentional unscrewing of the locking screw(s).

According to the invention, the "bore" which is provided in the sleeve is a bore as understood by the person skilled in the art. In addition, according to the invention, also a through hole which a person skilled in the art does not regard as a bore can be provided for receiving the locking screw or a section thereof. Such a through hole can, for example, be cast or can be a by-product of a casting process. In comparison to generating a bore, no sleeve material has to be ablated or removed upon casting. Such a non-bored through hole can further result from assembling several partial sleeve having corresponding gaps.

According to the invention, the term "locking" may be understood, for example, as a prevention of a movement—for example, a movement of the intramedullary nail—in a longitudinal axis thereof or about the longitudinal axis after completion of its insertion into the bone. In connection with the present invention, it is furthermore to be understood as a fixation of fracture fragments or other bone segments. The term "fixation" is also to be understood as the attempt to maintain the distance between the bone segments or fragments. Sintering, particularly a medically intended sintering of the bone fragments, during which the distance may be altered within a limited extent despite locking, is in this case not detrimental to the fixation. Hence, in the sense of the present invention, a locking screw or device can be embodied both as a device for fixating or fixing intramedullary nails and a device for securing at last two bones or segments or fragments thereof relative to each other. By designing an intramedullary nail according to the invention, minor misalignments in the position of the locking screw can be virtually automatically compensated during insertion of the locking screw in the intramedullary nail. Moreover, the surgeon has the possibility to vary the angle of the locking screw(s) penetrating through the intramedullary nail, e.g., with respect to the shaft and/or to vary the spatial alignment of the locking screw(s) even during the surgery, particularly when using a spherical sleeve which is freely alignable in three directions or degrees of freedom. Therefore, the surgeon has the possibility to precisely reposition, adapt, or compress the fracture fragments of the bone or the joint with respect to their anatomically correct positions.

The locking of the sleeve with the locking screw or the positional fixation or blockage of the sleeve can be realised by several different means. The sleeve, which is preferably made from a synthetic, resin or plastic material and which can—independently thereof—be provided with a slot similar to a dowel known in the art, can, for example, be expanded and fixed by a conical or otherwise suited design of the locking screw. Likewise, it is possible to achieve the said positional fixation of the sleeve with respect to the locking screw by a clamping screw which is positioned, for example, coaxially and/or substantially in parallel to the shaft of the intramedullary nail. Thus, such a clamping screw can, for example, also be embodied as or replaced by a fixing pin or a lockable device or any other device which can exert a compression or tension force on the sleeve in order to immobilise it in the spatial directions or in at least one plane. If several sleeves are provided in the intramedullary nail, these sleeves can be fixed, particularly fixed in a position and/or angle and/or location, by providing, for example, separating elements between the individual sleeves, wherein the individual sleeves are then fixed through a device such as, for example, a clamping screw. The invention also encompasses combinations of the previously described device and other devices of the aforementioned kind known to a person skilled in the art for achieving an arrest or a fixation.

However, provision of such a device—such as the separating elements—is not essential. Rather, in an alternative embodiment, sleeves being in direct contact with each other can be interlocked against each other.

The separating elements can be formed solid or with at least one cavity. These cavities can result in a greater deformation of the separating elements, which in turn increases the friction and thus the angular stability.

The separating elements can be designed such that they can be connected to the sleeve in a form closure connection like an indentation. In such a way, they can show a greater frictional resistance and thus increase the angular stability once being blocked.

The intramedullary nail according to the invention can be embodied as a modular structure in such a way that the intramedullary nail comprises a co-axial bore or opening in which an insert having at least one sleeve or a linked or combined unit of sleeves and separating elements can be inserted. This embodiment advantageously allows that, prior to the insertion of the insert, the opening is usable for a cannulation encompassing all advantages of cannulations known to a person skilled in the art.

The positioning of the locking screws is facilitated through an apparatus according to the invention by detachably connecting a bent guide curve to one end of the intramedullary nail. A positioning device is sliding on the guide curve, wherein the positioning device comprises an, in particularly linearly adjustable, aligning mechanism, which is alignable with the intramedullary nail and which is slideable in a plane comprising the centre plane of the intramedullary nail, and wherein the aligning mechanism is designed for receiving a locking screw or an instrument for inserting the locking device, e.g., for screwing in the locking screw, into the sleeve.

Preferably, the guide curve follows a track, for example a curve or an arc, in particular a circular segment, and is in particular provided with a substantially centrally located guideway which runs lengthwise and penetrates through the guide curve and is aligned with the intramedullary nail. A positioning device having the aligning mechanism, which is directed through the guideway and has an opening which is particularly aligned with the intramedullary nail and penetrates through the positioning device, slides in this guideway. The opening can further be extended by means of a co-axial guide tube.

The guide curve can follow a curve, it can however comprise curved or otherwise bent segments along with straight sections. The guide curve can also exclusively consist of straight sections without having any bent sections.

During explantation, the guide curve can be fixed to the intramedullary nail by means of the aforementioned coupling mechanisms in such a way that the removal (unscrewing) of the locking screws is facilitated by the guide curve and thus, the requirement of an intensive radiation exposure can be minimised. Due to the ability of precisely positioning the instruments with the help of the guide curve, the detectability of the screw heads of the locking screws will be facilitated. Thus, a minimally invasive removal of the implant without any radiation exposure can be effected.

By means of the sleeve which is movably supported in the shaft, the locking screw can be easily placed in the bore of the sleeve, wherein, particularly if several sleeves are provided for the fixation of individual fracture elements, markings or indentations or stops for the positioning device can be provided on the guide curve. Register marks or gratings can be provided on the guide curve in an axial and rotary direction.

Instead of locking screws, the sleeves can also be filled with placeholders. This has the advantage that a sleeve which is not occupied by or filled with a locking screw allows a desired distribution of force through or along the sleeve by means of the placeholder, when the axial tensioning is used to achieve an angularly stable fixation after completion of the insertion of the intramedullary nail in the bone.

Further embodiments of the invention are subject-matters of the dependent claims.

It is to be noted that the intramedullary nail according to the invention can be employed with one or several locking screws. Hence, the terms "locking screw" and "locking screws" can be used interchangeably in the present description. Whenever the term "locking screw" is used, it is to be understood that "locking screws" can be used as well, and vice versa, whenever this is technically possible. Also, the term "locking screw" is meant to be a locking device in its general meaning.

Therefore, the locking screw can moreover be formed as a locking pin. According to the invention, a thread is not required. The provision of a fit or any other device for increasing the friction between the sleeve and the locking screw can advantageously prevent an undesired longitudinal egression of the locking screw out of the sleeve in the course of time. These devices for increasing friction can thereby be provided solely over a section (or optionally along the section) of the sleeve and/or of the locking screw or over the whole length thereof.

The object according to the invention is also solved by a particularly lockable bone nail, in particular an intramedullary nail, for the treatment of a hollow bone as set forth in the instant claims. This bone nail comprises a shaft having a longitudinal axis wherein particularly the shaft comprises at least one opening for the insertion, e.g., for the introduction in or guidance through, at least one locking device. In a preferred embodiment according to the invention, the locking device can particularly be formed as a locking screw or locking pin.

The intramedullary nail comprises at least one receiving device—like, for example, the sleeve described above for receiving at least one section of the locking device wherein the receiving device is arranged alignably, particularly pivotably, in at least one of its spatial axes with respect to the longitudinal axis of the bone and/or of the intramedullary nail, and wherein its alignability with respect to the longitudinal axis can be inhibited, particularly by means of an arresting device. The term "alignment" is also to be understood as an alignment of the locking device with respect to the receiving device and/or to the bone and/or to the intramedullary nail.

According to the invention, the terms "inhibition" or "inhibiting" are to be understood as a termination of the alignability of the locking device, e.g., a locking screw, which has been inserted into the receiving device, in at least one spatial or rotational direction. This can be achieved by means of blocking, arresting, curing or hardening, locking or similar of the receiving device. Hereto, an inhibiting device such as the previously described clamping screw can be provided. The term "inhibition" can, however, also describe an effect or a characteristic which is inherently comprised by one of the structures. An example for this is the curability or the ability to harden, respectively, of a receiving device formed by means of cement.

A further example of how the alignability of the receiving device can be inhibited according to the invention is the provision of a device for increasing the friction between the locking device and the bone nail, wherein an insertion of the locking device (such as, e.g., by screwing, knocking in, sliding in or similar) into the receiving device incrementally or abruptly terminates the alignability of the receiving device. This can be achieved by spreading the receiving device by means of, for example, the tapered shaft of the locking device. By such a spreading or even by a corresponding pressure increase accompanied by deformation of an outer contour of the receiving device or by at least increasing the pressure exerted by the receiving device on its proximity, the receiving device can be pressed against another structure of the intramedullary nail in such a way that the receiving structure is blocked in its mobility and in particular in its alignability with respect to the intramedullary nail. The receiving means can thus solely be arrested by knocking in the locking device into the receiving device.

The locking device (e.g. in pin or screw form) can be designed such that the insertion of the section of the locking device which is to be inserted last in the receiving device effects the blocking. The locking device can be prepared for such a blockage. The receiving device can also be designed correspondingly. In addition, both the locking device and the receiving device can be formed for achieving the blockage or locking, respectively.

The bone nail as set forth in the instant claims can be combined with all features which are disclosed in the present application and which can for a person skilled in the art apparently be combined with a corresponding intramedullary nail.

The object according to the invention is further solved by an apparatus (aligning instrument) for fixing a locking intramedullary nail in a bone by means of at least one locking device.

The apparatus comprises a connecting device for detachably connecting the apparatus with a section of the locking intramedullary nail. Furthermore, it features a guide curve having a reception for receiving the locking device in order to position the locking device relative to the locking intramedullary nail.

The reception is arranged at the guide curve in such a way as to be adjustable between at least two positions so that the locking device received by the reception is alignable in at least a first angle or in a second angle different from the first angle relative to the intramedullary nail in order to be inserted into the intramedullary nail.

The above apparatus can be combined with all features which are disclosed in the present application and which are apparently combinable with a corresponding apparatus for a person skilled in the art.

All devices according to the invention can be manufactured from a type II anodised titanium alloy (Ti6A14V) for improved biomechanical and biomedical engineering properties.

By means of the present invention, prior to the screw positioning, also drills, spikes or guide wires or other tools can advantageously be inserted in an aligned, positioned and/or guided manner with the help of the aligning instrument or the apparatus having the guide curve.

Furthermore, an optionally necessary "removal of the metal", i.e. locating and unscrewing of the screws used at a later point of time, can be facilitated with the help of the aligning bracket. Also, the intramedullary nail can be coupled in an axial direction by the use of the apparatus according to the invention (as well as the aligning bracket) whereby a removal of the implant from the medullary cavity is enabled or facilitated.

BRIEF DESCRIPTION OF THE DRAWINGS

The invention will in the following be explained in more detail with the help of the drawings, wherein.

DETAILED DESCRIPTION OF THE INVENTION

Figure 1:
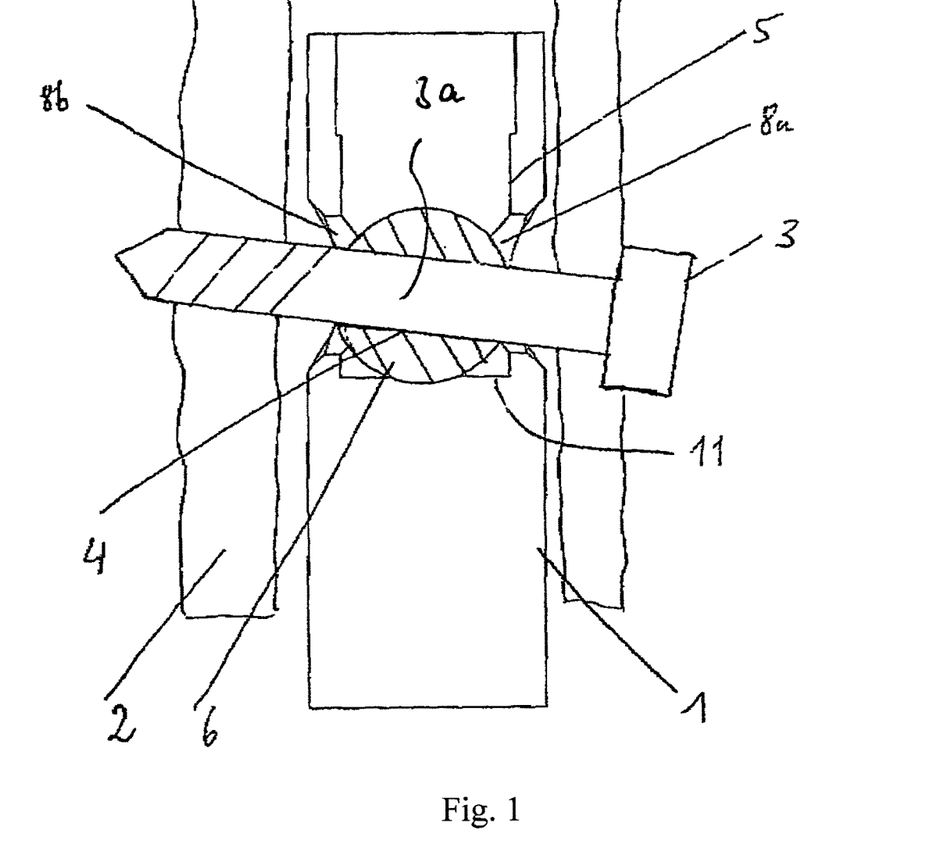
FIG. 1 shows an intramedullary nail according to the invention having a sleeve which is pivotably arranged in the shaft of the intramedullary nail and receives a locking screw for fixing the intramedullary nail.

FIG. 1 shows an intramedullary nail 1 that is implanted in the medullar cavity of a bone 2. In the intramedullary nail 1, in the area in which locking screw 3 is to be placed, a spherical formed sleeve 6 having a bore 4 for receiving a locking screw 3, is inserted in a shaft 5 of the intramedullary nail 1. The shaft 5 has two through holes 8a, 8b opposite to each other in the area of the sleeve 6, through which the locking screw 3 can be guided, whereby section 3a will come to rest in sleeve 6. The sleeve 6 rests on a seating 11 in the intramedullary nail 1 and is supported in a freely rotatable manner in shaft 5. Through this, the locking screw 3 can be pushed through the bore 4 in the intramedullary nail 1 in an arbitrary inclination in an angular range limited by the through holes 8a, 8b, in shaft 5 during the surgery. Also, small misalignments of the sleeve 6 or the locking screw 3 will be compensated, so that the locking screw 3 always engages in bore 4 of the sleeve 6.

By means of the angular flexibility or alignability during the insertion of the locking screw(s) 3, there is the possibility to adapt the intramedullary nail 1 during the implantation in an optimal manner to the individual anatomical or pathological situation of the patient.

The locking of the sleeve 6 in the shaft 5 can be realised in different ways.

Figure 2:
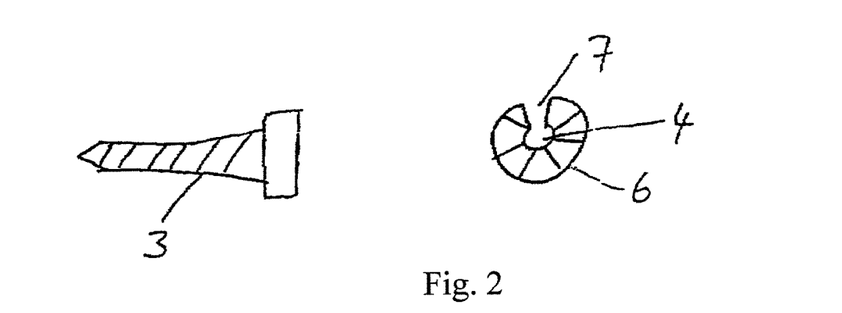
FIG. 2 shows a schematic representation of a locking screw and a sleeve for locking the intramedullary nail in a bone.

An example is shown in FIG. 2. The locking screw 3 has in this case a partially or completely conically formed screw shaft 3a; the sleeve 6 having its bore 4 is provided with a slot 7, similar to a dowel. The sleeve 6 is then expanded by screwing in the locking screw 3 and is anchored in the shaft 5 of the intramedullary nail 1. The sleeve is then held against corresponding stops, for example the edges of the through holes 8a and 8b. Through this frictional connection of the spherical sleeve 6 in shaft 5, the locking screw 3 will be permanently locked in the selected position in an angularly stable manner.

To achieve an optimal fixation, the sleeve 6 can be composed of an appropriately expandable material, for example, a synthetic or plastic material suitable for this application or comprise such a material.

Figure 3:
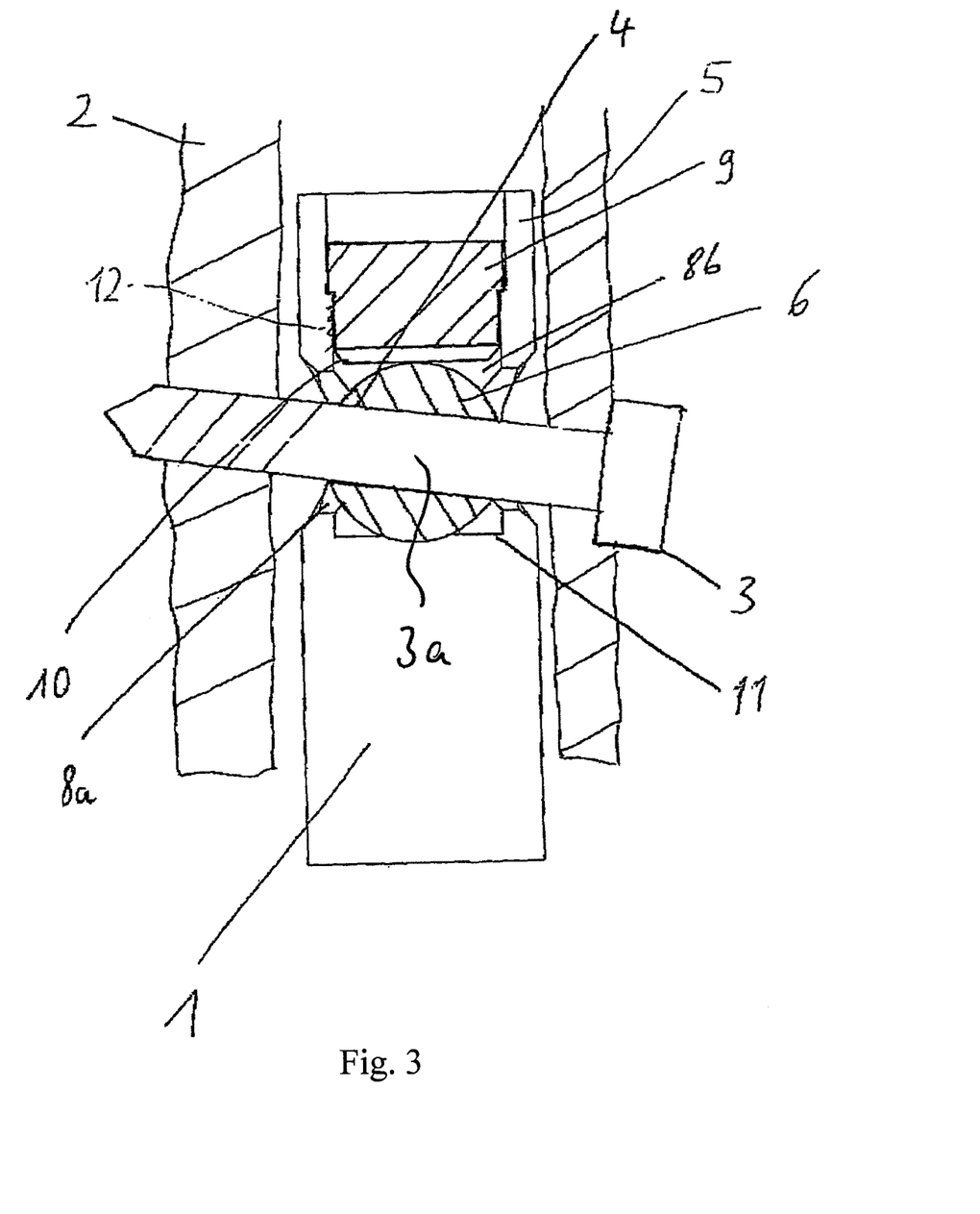
FIG. 3 shows an intramedullary nail implanted in the medullary cavity of a bone comprising a clamping screw for fixing the intramedullary nail in a positionally stable manner.

FIG. 3 shows another possibility for the angularly stable arresting of sleeve 6 with the locking screw 3. The design of the intramedullary nail 1, the sleeve 6 and the locking screw 3 is similar to that shown in FIG. 1. The spherically formed sleeve 6 can hereby in turn consist of a suitable synthetic or plastic material. The spherical or sleeve 6, respectively, rests upon a seating 11 in the shaft 5 of the intramedullary nail.

Above the spherical or the sleeve 6, respectively, shaft 5 is provided with a thread 12 in which a clamping screw 9 is inserted coaxially to the shaft, wherein the clamping screw 9 rests upon the upper side of sleeve 6. By screwing in the clamping screw 9 in thread 12, the sleeve 6 is pressed against the seating 11 and is thus fixed in a positionally stable manner after insertion of the locking screw 3.

For increasing the clamping force and the loosening torque of the sleeve 6 in shaft 5 resulting therefrom, the clamping screw 9 can be fitted with the sleeve 6 in a suitably geometrical manner on its contact area, which is, however, not shown here. Thereby, the static friction between the clamping screw and the sleeve can be increased.

In addition, the contact area of the clamping screw can be roughened, for example, through knurling or applying friction increasing coatings. Another possibility would be to provide the clamping screw 9 with a pointed tip, which will penetrate into the sleeve 6 and hence effect an additional frictional connection of the sleeve 6.

Figure 4:
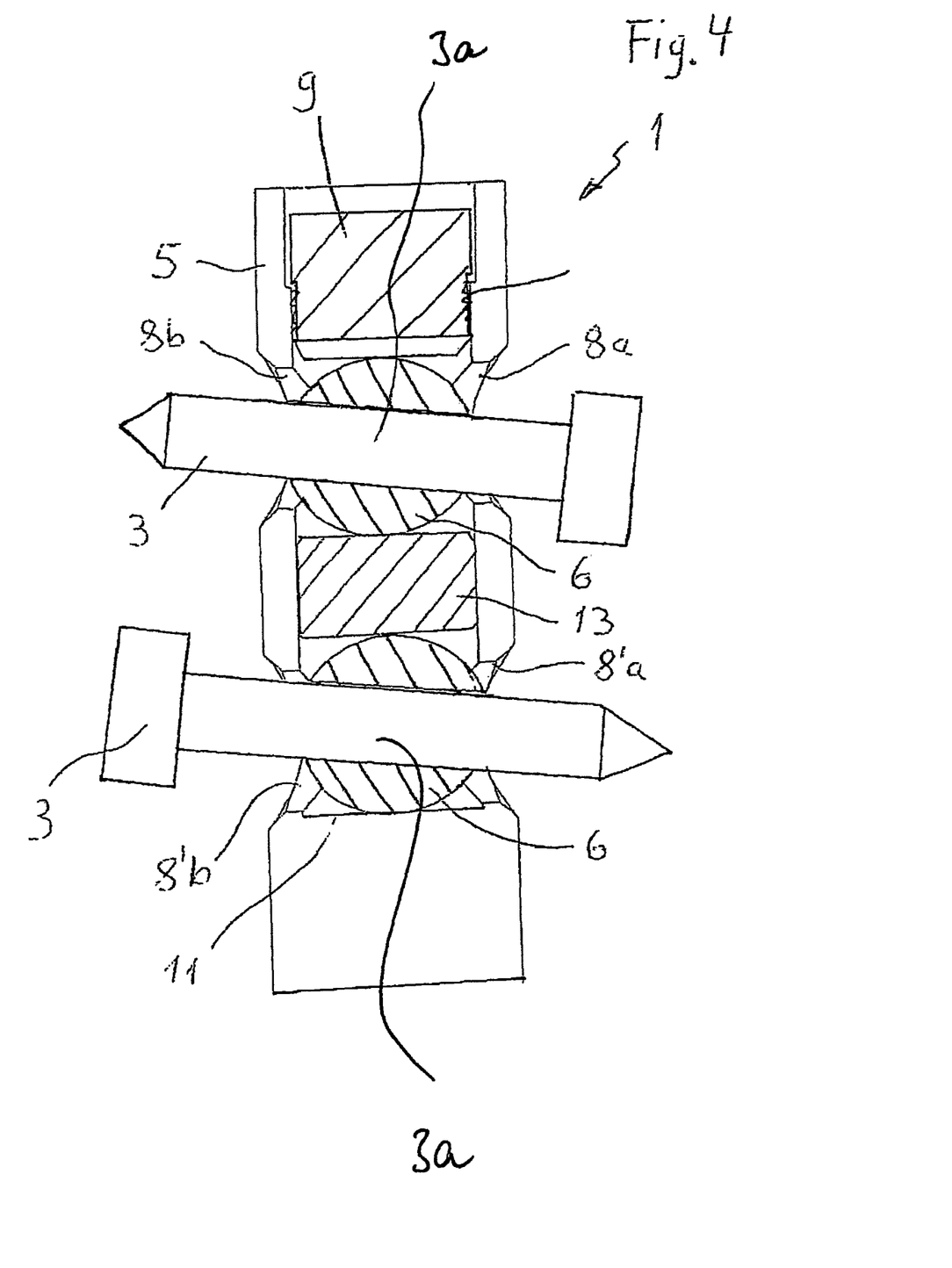
FIG. 4 shows a cross-section through an intramedullary nail comprising two sleeves which are each formed for receiving a locking screw and which are fixed to each other by a separating element and a clamping screw.

FIG. 4 shows an intramedullary nail 1 having shaft 5 which comprises several, in this case 2, through holes 8a, 8b and 8'a, 8'b, wherein a sleeve 6 is inserted in each of these areas through each of which a locking screw 3 can be pushed through.

For locking the two sleeves 6, a clamping screw 9 according to FIG. 3 which abuts against the upper sleeve 6 is provided again. Between the two sleeves 6 a block shaped separating element 13 is provided which abuts against both sleeves 6. By means of tightening the clamping screw 9, both sleeves 6 will be fixed in a positionally stable manner through the interconnection of the separating element 13.

Figure 5:
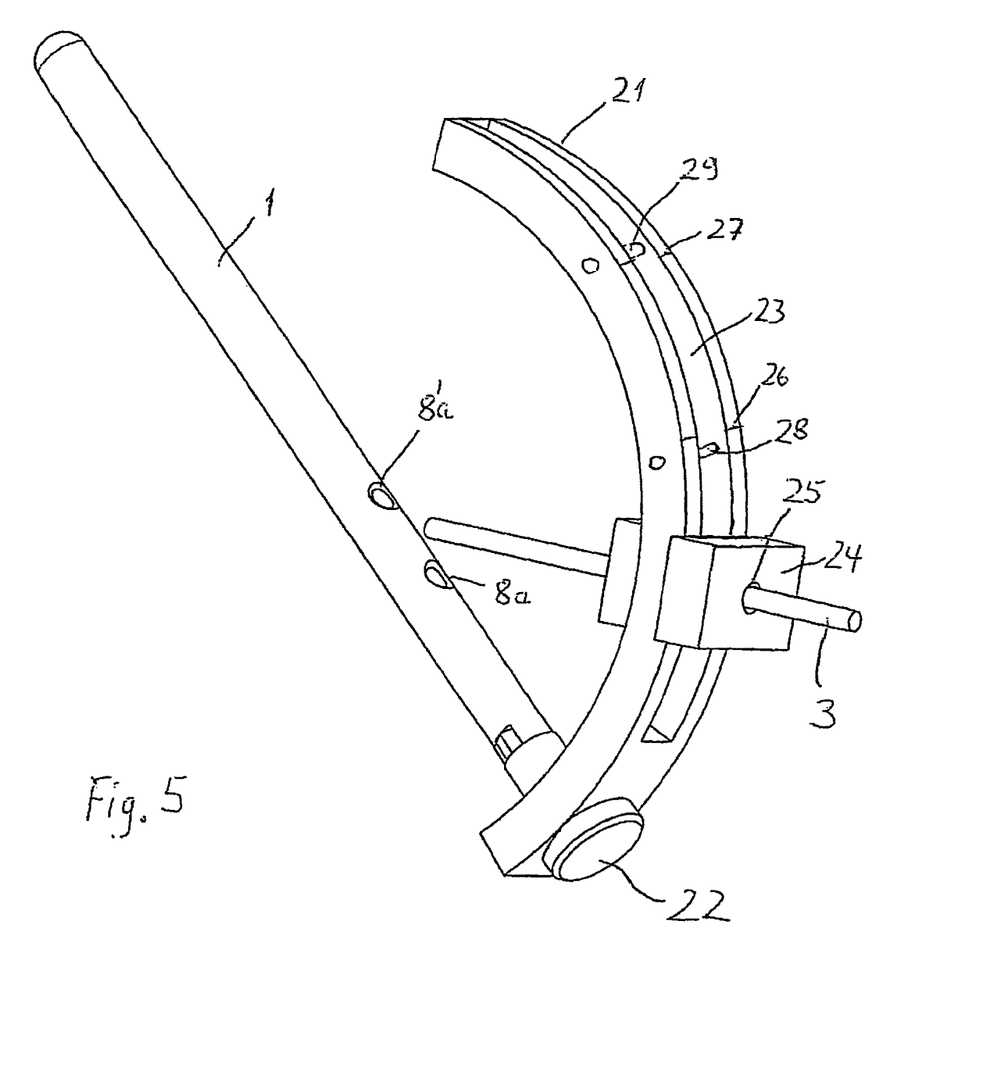
FIG. 5 shows a perspective view of an apparatus for facilitating the fixation of an intramedullary nail in a bone or a joint.

FIG. 5 shows an intramedullary nail 1 according to the invention with two through holes 8a and 8'a, in which spherical formed sleeves (not shown here) are inserted. A bent guide curve 21 which—in this case—follows a circular segment, is detachably connected to the upper end of the intramedullary nail with the use of a screw 22. The guide curve 21 is able to be rotated about the longitudinal axis of the intramedullary nail and can be fixed in the desired angular position by means of screw 22. The guide curve 21 has a guideway 23 which runs lengthwise and is substantially positioned centrally and penetrates through guide curve 21. The side walls of the guideway 23 are aligned to the intramedullary nail 1, a positioning device 24 having a central opening 25, into which a locking screw 3 can be inserted, slides in the guideway 23 in a frictional connection, and wherein the locking screw 3 is aligned with the centre plane of the intramedullary nail 1. In place of the locking screw 3, a guide tube can be inserted in the opening 26 first, before the locking screw will be inserted.

Prior to the insertion of the intramedullary nail, the positioning device 24 is displaced to a first position in which the intramedullary nail 1 or the guide tube, respectively, is aligned with a penetration or a through hole, e.g. through hole 8a. The position of the positioning device on the guide curve 21 can, for example, be marked with a marking 26. Subsequently, the positioning device 24 can be brought into a second position in which it is aligned with the through hole 8'a. This position can also be marked by means of a marking 27 on the guide curve 21.

Instead of providing the markings 26 or 27, respectively, it is possible to push a rod-shaped bar 28 or 29, respectively, through the guide curve 8 at against which the positioning device 24 will abut in the corresponding positions. Hereby, a surgeon can determine the desired angular position of the locking screw 3 which shall be screwed into the intramedullary nail 1.

What is claimed is:
1. A locking intramedullary nail for insertion into a medullary cavity of a hollow bone and for supporting bone fractures and reinforcing or stiffening joints, respectively, wherein the nail comprises an elongated shaft having a longitudinal axis, first and second successive through holes for receiving first and second respective locking screws therethrough, a first sleeve received and supported in the first through hole, a second sleeve received and supported in the second through hole, and at least one supporting element arranged between the first and second through holes, wherein the supporting element abuts against the sleeves; wherein each of the sleeves are pivotable in a direction perpendicular to the longitudinal axis, and comprise a bore for receiving the first and second locking screws, respectively, therein; wherein the sleeves are configured to lock the respective first and second locking screws in a positionally stable manner, and wherein the sleeves compress, block, and/or arrest each other by a force of a clamping screw.

2. The intramedullary nail of claim 1, wherein at least one of the sleeves comprises a roller having a roller axis which is perpendicular to a longitudinal axis of the shaft of the intramedullary nail.

3. The intramedullary nail of claim 1, wherein at least one of the sleeves is spherical and is arranged to freely pivot or rotate in more than one spatial axis.

4. The intramedullary nail of claim 1, wherein a clamping screw is arranged at least one of coaxially to the shaft of the intramedullary nail and substantially in parallel to a longitudinal axis of the intramedullary nail.

5. The intramedullary nail of claim 1, wherein at least one of the sleeves comprises or consists of synthetic or plastic material.

\* \* \* \* \*